United States Patent
Groth et al.

(10) Patent No.: US 11,091,431 B2
(45) Date of Patent: Aug. 17, 2021

(54) CONTINUOUS DILUTION OF POLYISOCYANATES

(71) Applicant: Covestro Deutschland AG, Leverkusen (DE)

(72) Inventors: Stefan Groth, Leverkusen (DE); Ruiwen Wu, Leverkusen (DE); Antonio Midolo, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/623,423

(22) PCT Filed: Jul. 2, 2018

(86) PCT No.: PCT/EP2018/067787
§ 371 (c)(1),
(2) Date: Dec. 17, 2019

(87) PCT Pub. No.: WO2019/007895
PCT Pub. Date: Jan. 10, 2019

(65) Prior Publication Data
US 2020/0115328 A1 Apr. 16, 2020

(30) Foreign Application Priority Data

Jul. 5, 2017 (EP) .................................... 17179716
Apr. 27, 2018 (EP) .................................... 18169695

(51) Int. Cl.
*C07C 263/16* (2006.01)

(52) U.S. Cl.
CPC .................. *C07C 263/16* (2013.01)

(58) Field of Classification Search
CPC .... C07C 263/16; C07C 263/18; C07C 263/20
USPC ........................................................ 560/336
See application file for complete search history.

(56) References Cited

U.S. PATENT DOCUMENTS

| 3,996,223 A | 12/1976 | Gupta et al. |
| 4,255,569 A | 3/1981 | Muller et al. |
| 4,419,513 A | 12/1983 | Breidenbach et al. |
| 5,086,175 A * | 2/1992 | Minato ............... C08G 18/8064 524/101 |
| 5,606,004 A | 2/1997 | Brahm et al. |
| 5,723,564 A | 3/1998 | Schmalstieg et al. |
| 6,936,678 B2 | 8/2005 | Brahm et al. |
| 2018/0008709 A1 | 1/2018 | Bakhoum et al. |

FOREIGN PATENT DOCUMENTS

| CN | 105001701 A | 10/2015 |
| DE | 870400 C | 3/1953 |
| DE | 951168 C | 10/1956 |
| DE | 953012 | 11/1956 |
| DE | 1013869 A | 8/1957 |
| DE | 1090196 B | 10/1960 |
| EP | 2174967 B1 | 2/2013 |

OTHER PUBLICATIONS

International Search Report, PCT/EP2018/067787, dated Oct. 1, 2018, Authorized officer: Carmen Österle.
S.A.P.I.C.I. Spa., Polurene HR.B.S., www.twanfong.com/product/01_hardener/01-11/HR.B.S.pdf, Feb. 1, 2010.
S.A.P.I.C.I. Spa., Polurene OK-HP, www.palmerholland.com/Assets/User/Documents/Product/43997/3175/MITM08281.pdf, Jan. 14, 2013.
S.A.P.I.C.I. Spa., Polurene 3031, www.twanfong.com/product/01_hardener/01-11/3031.pdf, Jan. 1, 2010.
Vencorex Chemicals, Easaqua X L 600, www.vencorex.com/wp-content/uploads/2016/05/PDS-Easaqua%E2%84%A2-X-L-600-March-2016-ENG.pdf, Mar. 2016.

* cited by examiner

Primary Examiner — Yong L Chu
(74) Attorney, Agent, or Firm — John E. Mrozinski, Jr.

(57) ABSTRACT

The invention relates to a process for producing a polyisocyanate composition comprising addition of at least one isocyanate-inert solvent to at least one polyisocyanate, characterized in that the addition of the solvent is carried out in one or more stages and at least one of these stages is performed as a continuous dilution. The invention further relates to the polyisocyanate compositions obtainable by the process, to the use of the polyisocyanate compositions, to a two-component system containing the polyisocyanate composition and to composite systems produced with the two-component system.

11 Claims, No Drawings

CONTINUOUS DILUTION OF POLYISOCYANATES

CROSS REFERENCE TO RELATED APPLICATIONS

This application is a national stage application under 35 U.S.C. § 371 of PCT/EP2018/067787, filed Jul. 2, 2018 which claims benefit of European Application No. 17179716.0 filed Jul. 5, 2017, and European Application No. 18169695.6 filed Apr. 27, 2018, all of which are incorporated by reference herein.

FIELD OF THE INVENTION

The present invention relates to a process for producing a polyisocyanate composition, in particular a polyisocyanate composition of tolylene diisocyanate, and to the polyisocyanate compositions obtainable therefrom. The invention further relates to the use of the polyisocyanate composition as a crosslinking agent in paints and adhesives and to the use of a continuous dilution. The present invention further relates to a two-component system containing the polyisocyanate composition and to the composite systems obtainable therefrom.

BACKGROUND OF THE INVENTION

Urethane-containing polyisocyanates composed of polyhydroxy compounds and tolylene diisocyanate have long been known and are described for example in DE 870 400, DE 953 012 and DE 1 090 196.

Isocyanurates of tolylene diisocyanate are produced by cyclic trimerization using various catalysts. Such reaction products have likewise long been known and are described for example in DE 951168 B, DE 1013869 A, U.S. Pat. No. 6,936,678 B2, DE 19523657 A1, U.S. Pat. No. 4,255,569 A, EP 2 174 967 B1 and CN 105001701.

It has long been desirable to produce low-viscosity but also high-functionality isocyanurates of tolylene diisocyanate. Tolylene diisocyanate is hereinbelow also referred to as TDI.

A low viscosity is desirable for example to improve the application characteristics of paints and adhesives. Furthermore the use of low-viscosity polyisocyanates as crosslinkers of paints and adhesives allows the solvent content of the formulation to be reduced. This means that the emissions of volatile organic compounds from such formulations can be reduced without a negative effect on usability.

It is also desirable in the use of such polyisocyanates as crosslinkers in paints and adhesives for the polyisocyanates to have a high content of isocyanate groups. This further increases sustainability in terms of a low content of organic solvents and rapid crosslinking, i.e. high process efficiency.

It is also desirable for the isocyanurates of TDI to have a low content of free diisocyanate. Due to the toxicological concerns around monomeric TDI this is an important condition for universal applicability in industrially applied paints and adhesives.

As is known from DE 951168B and DE 1013869A, the reaction of TDI to polyisocyanurate affords very high viscosity resins which impedes processing or makes it necessary to employ larger amounts of organic solvents. In addition polyisocyanates of TDI have a high tendency to crystallize and are only sparingly soluble in organic solvents.

A further important parameter is the solubility of the oligomeric isocyanurate in commonly used organic solvents. Incomplete solubility results in cloudy solutions which severely limits applicability in paint or adhesive formulations.

DETAILED DESCRIPTION OF THE INVENTION

It is accordingly an object of the present invention to provide a process for producing a polyisocyanate composition which makes it possible to obtain polyisocyanate compositions which have a low viscosity coupled with the highest possible content of isocyanate groups. The polyisocyanate compositions shall additionally have the lowest possible color number.

This object has been achieved by a process for producing a polyisocyanate composition comprising addition of at least one isocyanate-inert solvent to at least one polyisocyanate, characterized in that the addition of the solvent is carried out in one or more stages and at least one of these stages is performed as a continuous dilution.

The process according to the invention makes it possible to produce polyisocyanate compositions which have greater clouding resistance compared to the prior art and are therefore also suitable for uses in which clear solutions are required. The field of application is further improved as a result of the polyisocyanate compositions having a color number of <100 Hazen, preferably <95 Hazen. The color number in Hazen is determined according to DIN EN 1557:1997-03.

The present invention therefore also provides in an advantageous embodiment a process for producing a polyisocyanate composition having a color number of <100 Hazen, preferably <95 Hazen, determined according to DIN EN 1557:1997-03 comprising the addition of at least one isocyanate-inert solvent to at least one polyisocyanate, characterized in that the addition of the solvent is carried out in one or more stages and at least one of these stages is performed as a continuous dilution.

In a first preferred embodiment the polyisocyanate is a polyisocyanate based on at least one aliphatic, cycloaliphatic, araliphatic or aromatic diisocyanate, preferably composed of an araliphatic or aromatic diisocyanate and particularly preferably composed of an aromatic diisocyanate. The term composed of a diisocyanate is equivalent to based on such a diisocyanate.

Suitable aliphatic, cycloaliphatic, araliphatic or aromatic diisocyanates are for example selected from the group consisting of 1,4-diisocyanatobutane, 1,5-diisocyanatopentane (PDI) 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 2,4- and 2,6-diisocyanato-1-methylcyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane, 2,4'-diisocyanatodicyclohexylmethane, 1-isocyanato-1-methyl-4(3)isocyanatomethylcyclohexane, bis(isocyanatomethyl)norbornane, 1,3- and 1,4-bis(isocyanatomethyl)benzene (XDI), 1,3- and 1,4-bis(2-isocyanatoprop-2-yl)benzene (TMXDI), tolylene diisocyanate (TDI), 2,4'- and 4,4'-diisocyanatodiphenylmethane (MDI), 1,5-diisocyanatonaphthalene, 1,3- and 1,4-phenylene diisocyanate or any desired mixtures of such diisocyanates.

Particularly preferred are 1,5-diisocyanatopentane (PDI), 1,6-diisocyanatohexane (HDI), 1,3- and 1,4-diisocyanatocyclohexane, 2,4- and 2,6-diisocyanato-1-methylcyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane, 2,4'-diisocyanatodicyclohexylmethane, 1,3- and 1,4-bis(isocyanatomethyl)benzene (XDI), tolylene diisocyanate (TDI), 2,4'- and 4,4'-diisocyanatodiphenylmethane (MDI) or 1,5-diisocyanatonaphthalene.

It is a specific object of the present invention in particular to provide a process for producing a polyisocyanate composition composed of tolylene diisocyanate which makes it possible to obtain polyisocyanate compositions composed of tolylene diisocyanate which have a low viscosity coupled with the highest possible content of isocyanate groups and are additionally in the form of clouding-resistant solutions. The polyisocyanate compositions should additionally have the lowest possible color number.

This specific object has been achieved by a process for producing a polyisocyanate composition composed of tolylene diisocyanate comprising addition of at least one isocyanate-inert solvent to at least one polyisocyanate composed of tolylene diisocyanate, characterized in that the addition of the solvent is carried out in one or more stages and at least one of these stages is performed as a continuous dilution.

Thus in a further preferred embodiment the polyisocyanate is based on tolylene diisocyanate. The term "composed of tolylene diisocyanate" is equivalent to "based on tolylene diisocyanate".

The present invention also provides in an advantageous embodiment a process for producing a polyisocyanate composition composed of tolylene diisocyanate having a color number of <100 Hazen, preferably <95 Hazen, determined according to DIN EN 1557:1997-03, comprising the addition of at least one isocyanate-inert solvent to at least one polyisocyanate composed of tolylene diisocyanate, characterized in that the addition of the solvent is carried out in one or more stages and at least one of these stages is performed as a continuous dilution.

In the present application tolylene diisocyanate represents an umbrella term for the isomers 2,4-tolylene diisocyanate, 2,6-tolylene diisocyanate and any desired mixtures of 2,4- and 2,6-tolylene diisocyanate.

According to the invention references to "comprising", "containing" etc., are preferably to be understood as meaning "substantially consisting of" and especially preferably to be understood as meaning "consisting of".

In the present application "continuous dilution" is to be understood as meaning that at least two volume flows, preferably precisely two volume flows, are mixed with one another such that the dilution is effected substantially without a concentration trajectory. In the present application "substantially without a concentration trajectory" is to be understood as meaning that the solids content in the outflowing product stream may vary between ≤10% above and ≤10% below, preferably between ≤5% above and ≤5% below and particularly preferably between ≤2% above and ≤2% below the target solids content of the diluted product stream.

Suitable apparatuses for continuous dilution are for example T-pieces, dual-line systems comprising a static mixer and a vessel/intermediate dissolution vessel. In the present application a vessel/intermediate dissolution vessel is to be understood as meaning a container in which at least two volume flows are continuously added to a stirred volume from which the diluted product stream is accordingly discharged. This product stream is the polyisocyanate composition according to the invention and in the case of a plurality of dilution stages the product stream obtained after the last dilution stage is the polyisocyanate composition according to the invention.

It is preferable when the continuous dilution is carried out when at least two liquid streams, particularly preferably precisely two liquid streams, are continuously added to a stirred volume from which the diluted product stream is preferably continuously discharged. Such a stirred volume may for example be a vessel mentioned hereinabove. The two liquid streams are generally the polyisocyanate composed of TDI (polyisocyanate stream) for dissolution and the at least one isocyanate-inert solvent (solvent stream).

In contrast to the known batch dilution disadvantages during commixing may be very largely avoided in the process according to the invention since the desired concentration is always directly present. This also allows the residence time to be kept as short as possible which has an advantageous effect on the stability of the products.

Employable solvents include diluents and solvents commonly used in polyurethane chemistry such as for example toluene, xylene, cyclohexane, butyl acetate, ethyl acetate, ethyl glycol acetate, pentyl acetate, hexyl acetate, methoxypropyl acetate, tetrahydrofuran, dioxane, acetone, N-methylpyrrolidone, methyl ethyl ketone, white spirit, higher-substituted aromatics such as are commercially available for example under the designations Solvent Naphtha®, Solvesso®, Shellsol®, Isopar®, Nappar® and Diasol®, aromatic naphtha, tetralin, decalin and alkanes having more than 6 carbon atoms, customary plasticizers, such as phthalates, sulfonic esters and phosphoric esters, and mixtures of such diluents and solvents.

Suitable solvents further include polyisocyanates based on aliphatic diisocyanates such as are described in DE-A 4 428 107 for example. This makes it possible to obtain diluted low-monomer TDI trimers which contain little, if any, volatile solvent and diluent.

In a further preferred embodiment of the process according to the invention the addition of the solvent is carried out in at least two stages, wherein the first stage is performed as a continuous dilution. The at least second stage may be performed continuously or discontinuously. This results in the advantage that the clouding resistance of the polyisocyanate composition according to the invention is yet further increased. In addition, the color number too is further reduced.

It is also possible for a third, fourth, fifth or nth stage to be carried out, it being necessary here to weigh up the associated process engineering effort against the possible gain in further clouding resistance. It has been found that in most cases a two-stage addition provides the optimal balance of process engineering complexity and possible gain in further clouding resistance.

In a multistage addition, i.e. an addition comprising a plurality of stages, of at least one isocyanate-inert solvent, different dilution levels (solids contents) are achieved in the stages proceeding sequentially in different apparatuses, such as for example intermediate dissolution vessels. These dilution levels are hereinbelow also referred to as solids contents. In the present application solids content is to be understood as meaning the weight fraction of the polyisocyanate in the polyisocyanate composition.

In a further preferred embodiment of the process according to the invention a solids content of ≥30% to ≤90% by weight, preferably ≥50% to ≤85% by weight, particularly preferably ≥55% to ≤75% by weight and very particularly preferably ≥60% to ≤70% by weight is established in the first stage.

In this at least two-stage addition it is further preferred when a solids content of ≥10% to ≤80% by weight, preferably ≥15% to ≤65% by weight, particularly preferably ≥20% to ≤50% by weight and very particularly preferably ≥25% to ≤35% weight is established in the second stage, wherein the solids content established in the first stage is reduced by at least 15% by weight, preferably by at least 25% by weight, in the second stage. This results in the advantage that the at least two-stage addition makes it possible to establish solids contents that have the broadest possible suitability for a later application of the polyisocyanate composition obtainable by the process according to the invention while still being clouding-resistant.

In a further preferred embodiment of the process according to the invention the polyisocyanate is produced from tolylene diisocyanate by
  (i) reaction of tolylene diisocyanate to form a polyisocyanate and
  (ii) removal of the unconverted tolylene diisocyanate.

In the context of the present invention the "removal of the unconverted tolylene diisocyanate" is to be understood as being substantially complete. The term "substantially complete" is preferably to be understood as meaning that residual contents of monomeric tolylene diisocyanate are ≤0.5% by weight, preferably ≤0.3% by weight and particularly preferably ≤0.1% by weight based on the total weight of the polyisocyanate composed of tolylene diisocyanate.

The removal of the unconverted tolylene diisocyanate in step (ii) may be carried out by any desired methods. However, it is preferable when the removal of the unconverted tolylene diisocyanate in step (ii) is carried out by means of at least one thermal separation process which may comprise one or more stages, preferably by means of at least one two-stage thermal separation process and particularly preferably by means of at least one falling film evaporator and/or at least one thin film evaporator. This results in the advantage that a sufficient removal of the unconverted tolylene diisocyanate is achievable even for relatively large throughputs.

Suitable thermal separation methods are for example distillations under vacuum using a thin film evaporator and/or a falling film evaporator. Generally suitable for the removal of TDI are pressures in the range of 0.1-20 mbar and temperatures of 120-250° C.

It is preferable when the thermal separation process is performed at a heating medium temperature of ≥140° C. to ≤235° C. and preferably of ≥160° C. to ≤215° C. This results in the advantage that the removal of the unconverted tolylene diisocyanate is carried out in a gentle yet efficient manner Depending on the process engineering effort contents of monomeric tolylene diisocyanate of ≤0.5% by weight, preferably ≤0.3% by weight and particularly preferably ≤0.1% by weight based on the total weight of the polyisocyanate composed of tolylene diisocyanate are realizable and the lower these contents the broader the field of application of the polyisocyanate composition according to the invention since occupational health, especially in manual applications, is yet further improved. The contents of unconverted tolylene diisocyanate are determinable by gas chromatography according to DIN EN ISO 10283:2007-11 with an internal standard.

If other diisocyanates from the abovementioned list are employed in addition to the tolylene diisocyanate or instead of the tolylene diisocyanate, the abovementioned residual contents and removal options relate to the altogether present residual contents of all monomeric diisocyanates and a person skilled in the art may undertake minor adaptations for example with regards to the process parameters to tailor the removal to the relevant monomeric diisocyanate to be removed.

In a further preferred embodiment step (i) of the process employs a mixture of 2,4- and 2,6-tolylene diisocyanate which consists of 2,4-tolylene diisocyanate to an extent of ≥50% to ≤99% by weight, preferably to an extent of ≥70% to ≤95% by weight and particularly preferably to an extent of ≥75% to ≤90% by weight based on the total weight of the employed tolylene diisocyanate. This results in the further advantage that a proportionate balance between selectivity of the isocyanate groups of varying reactivity in the 2,4-TDI and elevation of the crystallization resistance by at least a small proportion of 2,6-TDI is achieved.

Both 2,4- and 2,6-tolylene diisocyanate and mixtures thereof are generally commercially available. They are producible by known processes, for example by phosgenation of the corresponding tolylene diamine (TDA) in the liquid phase or the gas phase. Particular preference is given to tolylene diisocyanates produced by gas-phase phosgenation of TDA since such a process is particularly efficient.

In a further embodiment the polyisocyanate formed in step (i) of the process is a urethane-containing polyisocyanate composed of tolylene diisocyanate. This is preferably produced by reacting polyhydroxy compounds with 5 to 10 times the molar amount of TDI. Suitable low molecular weight polyhydroxy compounds are dihydric to tetrahydric alcohols having a molecular weight of 62 to 146 and/or polyether polyols, in pure form or as any desired mixtures, produced therefrom by addition of ethylene and/or propylene oxide.

Contemplated dihydric to tetrahydric alcohols include for example ethylene glycol, 1,2-propylene glycol, 1,3-propylene glycol, 1,2-butanediol, 1,3-butanediol, 1,4-butanediol, 1,5-pentanediol, neopentyl glycol, 1,6-hexanediol, 2-ethylhexanediol, glycerol, trimethylolpropane and pentaerythritol.

Suitable polyether polyols have a molecular weight calculable from hydroxyl group content and hydroxyl functionality of 106 to 600, preferably 106 to 470. It is preferable to employ polyether diols and polyether triols. These polyether polyols are obtainable in the manner known per se by alkoxylation of suitable difunctional to tetrafunctional starter molecules or suitable mixtures of starter molecules, wherein the alkoxylation especially employs propylene oxide and/or ethylene oxide, optionally in admixture or consecutively in any desired sequence. It is preferable when the abovementioned dihydric to tetrahydric alcohols are employed as starter molecules. It is very particularly preferable to employ mixtures of trimethylolpropane and diethylene glycol.

In a further preferred embodiment the polyisocyanate of the process according to the invention is an isocyanate-containing polyisocyanurate composed of tolylene diisocyanate, wherein the reaction of tolylene diisocyanate in step (i) to form isocyanurate groups is carried out in the presence of at least one catalyst and terminated at a content of isocyanate groups of ≥30% to ≤46% by weight, preferably of ≥34% to ≤44% by weight and particularly preferably of ≥38% to ≤42% by weight by addition of at least one catalyst poison.

In this embodiment the steps (i) and (ii) are preferably performed in the presence of ≥0% to <1% by weight of distillation aids that are inert under distillation conditions, liquid and have a boiling point at least 50° C. higher than that of tolylene diisocyanate and/or ≥0% to <1% by weight based on the total weight of the compounds employed in step (i) of compounds comprising one or more hydroxyl groups.

It is particularly preferable when such distillation aids are present in amounts of ≥0% to ≤0.5% by weight, preferably ≥0% to ≤0.25% by weight and particularly preferably ≥0% to ≤0.1% by weight based on the total weight of the compounds employed in step (i) and/or when the compounds comprising one or more hydroxyl groups are present in amounts of ≥0% to ≤0.8% by weight, preferably ≥0% to ≤0.5% by weight, particularly preferably ≥0% to ≤0.1% by weight, based on the total weight of the compounds employed in step (i). Distillation aids optionally present in these amounts and/or compounds comprising one or more hydroxyl groups optionally present in these amounts do not have a negative effect on the process according to the invention. However, it is very particularly preferable when in steps (i) and (ii) of the process according to the invention no distillation aids and/or no compounds comprising one or more hydroxyl groups are present with the exception of the optionally present aromatic hydroxyl groups recited hereinbelow as catalyst constituents.

In the case where isocyanate-inert solvents have been added in steps (i) to (ii) in the process according to the invention it is preferable when such solvents may be present in steps (i) to (ii) to an extent of ≥0% to ≤3% by weight, preferably ≥0% to ≤1% by weight and particularly preferably ≥0% to ≤0.05% by weight, based on the total weight of the compounds employed in step (i).

Contemplated catalysts for the formation of isocyanurate groups, also referred to hereinbelow as trimerization catalysts, in principle include all known catalysts of the prior art such as for example phosphines, alkali metal salts, alkali metal alkoxides, tertiary amines, fluorides, hydrogen difluorides or hydrogen polyfluorides. It is preferable to employ catalysts comprising aromatics-bonded N,N-dialkylaminomethyl groups and phenolic OH groups (alkyl: independent alkyl chain or alkylene chain having up to 18 carbon atoms optionally separated by oxygen or sulfur). These groups may be distributed over several molecules or may be positioned on one or more benzenic aromatics. It is particularly preferable when catalysts containing both hydroxyl and dialkylaminomethyl groups in one molecule are employed. It is very particularly preferable to employ catalysts whose dialkylaminomethyl groups (alkyl=$C_1$ to $C_3$ chain) are in the ortho position relative to aromatic hydroxyl groups. Examples include the following Mannich bases such as are obtainable for example on the basis of phenol, p-isononylphenol or Bisphenol A for example by reaction of 188 parts by weight of phenol with 720 parts of a 25% aqueous dimethylamine solution and 425 parts by weight of a 40% formaldehyde solution by heating to 80° C. for two hours, removal of the aqueous phases and distillation of the organic phase at 90° C./10 Torr according to DE-A 2 452 531 9.

The reaction in step (i) is generally carried out at temperatures between 20° C. and 120° C., preferably between 40° C. and 100° C. and particularly preferably between 60° C. and 90° C.

The catalysts are employed in step (i) as pure substance or dissolved optionally in a plurality of small portions, wherein the amount may be varied over a wide range. It is preferable when the amount of altogether employed catalyst is ≥0.001% to ≤2.0% by weight, preferably ≥0.003% to ≤0.5% by weight and particularly preferably ≥0.005% to ≤0.05% by weight based on the total weight of the compounds employed in step (i) and (ii).

The termination of the reaction in step (i) is carried out by addition of at least one catalyst poison, wherein employable catalyst poisons include for example sulfur (when phosphines are used as catalysts) or alkylating agents such as for example methyl toluenesulfonate (in the case of the preferred use of Mannich bases as catalysts) or else acylating agents such as for example benzoyl chloride.

The amount of catalyst poison to be employed is chosen according to the employed amount of catalyst, so that the catalyst is deactivated. It is preferable to employ an altogether subequimolar amount of the catalyst poison based on the equivalent of Lewis bases of the catalysts, though even≥20% to <100% based on the employed equivalent of Lewis base of the catalyst may be sufficient for complete deactivation of the catalyst.

Irrespective of which polyisocyanate composed of TDI is employed in the process according to the invention, in a further preferred embodiment addition of the at least one isocyanate-inert solvent to the at least one polyisocyanate, preferably composed of tolylene diisocyanate, is followed in a further step by addition of at least one polyisocyanate composition composed of tolylene diisocyanate which is distinct from the polyisocyanate of the preceding embodiments, preferably at least one polyisocyanurate composition composed of tolylene diisocyanate and/or at least one polyurethane composition composed of tolylene diisocyanate, and optionally by addition of one or more assistant and additive substances. This polyisocyanurate composition composed of tolylene diisocyanate and this polyurethane composition composed of tolylene diisocyanate are producible by known processes but also by the above-described processes for producing the isocyanate-containing polyisocyanurate composed of tolylene diisocyanate and the urethane-containing polyisocyanate composed of tolylene diisocyanate.

This results in the further advantage that the physical and chemical properties of mixtures containing at least one polyisocyanate according to the invention are specifically adjustable.

Suitable assistant and additive substances include for example the customary wetting agents, flow control agents, anti-skinning agents, antifoams, solvents, matting agents such as for example silica, aluminum silicates and high-boiling waxes, viscosity regulators, pigments, dyes, UV absorbers, and stabilizers against thermal/oxidative degradation.

The subject matter of the invention further includes a polyisocyanate composition produced or producible by the process according to the invention since it has surprisingly been found that such a process mode results in clouding-resistant compositions whereas an addition of solvent which does not have at least one stage performed as a continuous dilution results in cloudy compositions.

In this subject matter of the invention this preferably applies to polyisocyanate compositions where the polyisocyanate is based on 1,5-diisocyanatopentane (PDI), 2-methyl-1,5-diisocyanatopentane, 1,5-diisocyanato-2,2-dimethylpentane, 1,10-diisocyanatodecane, 2,4- and 2,6-diisocyanato-1-methylcyclohexane, 2,4'-diisocyanatodicyclohexylmethane, 1-isocyanato-1-methyl-4(3)isocyanatomethylcyclohexane, bis(isocyanatomethyl)norbornane, 1,3- and 1,4-bis(isocyanatomethyl)benzene (XDI), 1,3- and 1,4-bis(2-isocyanato-prop-2-yl)benzene (TMXDI), tolylene diisocyanate (TDI), 2,4'- and 4,4'-diisocyanatodiphenylmethane (MDI), 1,5-diisocyanatonaphthalene or 1,3- and 1,4-phenylene diisocyanate or mixtures of the abovementioned diisocyanates. It is particularly preferable when the polyisocyanate is based on 1,5-diisocyanatopentane (PDI), 2-methyl-1,5-diisocyanatopentane, 1,5-diisocyanato-2,2-dimethylpentane, 1,10-diisocyanatodecane, 2,4- and 2,6-diisocyanato-1-methylcyclohexane, 2,4'-diisocyanatodicyclohexylmethane, 1-isocyanato-1-methyl-4(3) isocyanatomethylcyclohexane, bis(isocyanatomethyl)norbornane, 1,3- and 1,4-bis(isocyanatomethyl)benzene (XDI), 1,3- and 1,4-bis-(2-isocyanato-prop-2-yl)benzene (TMXDI), tolylene diisocyanate (TDI), 2,4'- and 4,4'-diisocyanatodiphenylmethane (MDI), 1,5-diisocyanatonaphthalene or 1,3- and 1,4-phenylene diisocyanate and very particularly preferably composed of tolylene diisocyanate (TDI).

In addition to the advantageous clouding resistance the polyisocyanate compositions according to the invention have a very low color number of <100 Hazen, preferably <95 Hazen. The color number in Hazen is determined according to DIN EN 1557:1997-03.

The subject matter of the invention further includes the use of the continuous dilution in the dissolution of polyisocyanates, preferably of polyisocyanates composed of tolylene diisocyanate, for preventing cloudiness in the polyisocyanate composition.

The polyisocyanate composition according to the invention is very suitable for use as a crosslinking agent in an adhesive or in a coating material, preferably in an adhesive. This is therefore further included in the subject matter of the invention.

The polyisocyanate compositions producible by the process according to the invention are preferably used for producing adhesives or coating materials curable under the influence of atmospheric humidity. They may likewise be used for producing adhesion promoters, printing inks and molded polyurethane articles. It is particularly preferable when they are used as crosslinkers in two-component systems with isocyanate-reactive compounds that are known per se.

The subject matter of the invention therefore further includes a two-component system comprising an isocyanate component A) containing at least one polyisocyanate composition according to the invention and an isocyanate-reactive component B) containing at least one isocyanate-reactive compound, preferably at least one hydroxyl-containing polyester.

Suitable isocyanate-reactive compounds are for example hydroxy-functional polyethers, polyesters, polyamides, polycarbonates, polyacrylates, polybutadienes and hybrids of the recited hydroxy-functional polymers. Low molecular weight diols and polyols, dimer and trimer fatty alcohols and amino-functional compounds may also be used in the two-component system according to the invention. Cyclohexanone-formaldehyde condensates, for example in castor oil, are also suitable. However, hydroxyl-containing polyesters are particularly preferred. Additionally employable in the coatings or adhesives are other assistant and additive substances such as for example the customary wetting agents, flow control agents, anti-skinning agents, antifoams, adhesion promoters, solvents, matting agents such as for example silica, aluminum silicates and high-boiling waxes, viscosity regulators, pigments, dyes, UV absorbers, and stabilizers against thermal/oxidative degradation. The coating compositions may be used in the form of clearcoats and in the form of pigmented paints.

The obtained coating materials or adhesives may be used for coating or adhesive bonding of any desired substrates such as for example natural or synthetic fibers, preferably wood, plastics, leather, paper, textiles, glass, ceramics, plaster, masonry, metals or concrete and particularly preferably paper or leather. They may be applied with customary application methods such as spraying, spreading, flow coating, curtain coating, immersing, or roller application.

The subject matter of the invention therefore further includes a composite system produced or producible by curing the two-component system according to the invention applied to at least one substrate.

The invention is more particularly elucidated hereinbelow with reference to examples and comparative examples but without restriction thereto.

EXAMPLES

All reported percentages are based on weight unless otherwise stated.

The NCO contents were determined by titrimetry according to DIN EN ISO 11909:2007-05.

The residual monomer contents were measured according to DIN EN ISO 10283:2007-11 by gas chromatography with an internal standard.

Cloudiness was determined according to DIN EN ISO 7027-1:2016.

Example 1 (Noninventive)

1500 g of a tolylene diisocyanate isomer mixture composed of about 80% 2,4-tolylene diisocyanate and 20% 2,6-tolylene diisocyanate are initially charged in a 2 L flask at 80° C. 0.52 g of a Mannich base (bisphenol/formaldehyde/dimethylamine 25% in butyl acetate/xylene 19:56) is then added over 2 hours with stirring while maintaining a temperature of 78-82° C. Once an NCO content of 40.4% is achieved 1 g of dibutyl phosphate is added to terminate the reaction. The excess diisocyanate is then continuously removed from the thus obtained crude product by distillation at temperatures of 180° C. and a pressure of 0.05 mbar. The obtained hot resin (370 g) is conveyed directly to 863 g of boiling ethyl acetate in a stirred flask fitted with a reflux cooler using a pump which corresponds to a one-stage, discontinuous dilution from 100% solids content to 30% solids content. This affords a solution having the following properties:
NCO: 7.1%
Monomer content: 0.08%
Cloudiness: 21 NTU Example 2 (Inventive)

1500 g of a tolylene diisocyanate isomer mixture composed of about 80% 2,4-tolylene diisocyanate and 20% 2,6-tolylene diisocyanate are initially charged in a 2 L flask at 80° C. 0.52 g of a Mannich base (bisphenol/formaldehyde/dimethylamine 25% in butyl acetate/xylene 19:56) is then added over 2 hours with stirring while maintaining a temperature of 78-82° C. Once an NCO content of 40.4% is achieved 1 g of dibutyl phosphate is added to terminate the reaction. The excess diisocyanate is then continuously removed from the thus obtained crude product by distillation at temperatures of 180° C. and a pressure of 0.05 mbar. The hot resin discharged from the distillation is conveyed directly at 105 g/h into a stirred 500 ml 4-necked flask fitted with a reflux cooler using a pump. 245 g/h of ethyl acetate are simultaneously added from a dropping funnel and the continuously diluted product is continuously transferred at 350 g/h into a cooled receiver flask via a submerged riser tube using a pump. The contents of the 4-necked flask remain constant at about 400 g and have a temperature of about 80° C. This affords a solution having a solids content of 30% and the following properties:
NCO: 7.0%
Monomer content: 0.03%
Cloudiness: 12 NTU Example 3 (Inventive)

1500 g of a tolylene diisocyanate isomer mixture composed of about 80% 2,4-tolylene diisocyanate and 20% 2,6-tolylene diisocyanate are initially charged in a 2 L flask at 80° C. 0.52 g of a Mannich base (bisphenol/formaldehyde/dimethylamine 25% in butyl acetate/xylene 19:56) is then added over 2 hours with stirring while maintaining a temperature of 78-82° C. Once an NCO content of 40.4% is achieved 1 g of dibutyl phosphate is added to terminate the reaction. The excess diisocyanate is then continuously removed from the thus obtained crude product by distillation at temperatures of 180° C. and a pressure of 0.05 mbar. The hot resin discharged from the distillation is conveyed directly at 105 g/h into a stirred 500 ml 4-necked flask fitted with a reflux cooler using a pump. 57 g/h of ethyl acetate are simultaneously added from a dropping funnel and the continuously diluted product is continuously transferred at 162 g/h into a cooled receiver flask via a submerged riser tube using a pump. The contents of the 4-necked flask remain constant at about 400 g and have a temperature of about 80° C.

The contents of the receiver flask are subsequently diluted to 30% solids content with ethyl acetate in a discontinuous step. This affords a solution having the following properties:
NCO: 7.0%
Monomer content: 0.05%
Cloudiness: 2 NTU Various aspects of the subject matter described herein are set out in the following numbered clauses:

Clause 1. A process for producing a polyisocyanate composition comprising addition of at least one isocyanate-inert solvent to at least one polyisocyanate, characterized in that the addition of the solvent is carried out in one or more stages and at least one of these stages is performed as a continuous dilution.

Clause 2. The process as in Clause 1, characterized in that the polyisocyanate is based on at least one aliphatic, cycloaliphatic, araliphatic or aromatic diisocyanate, preferably composed of an araliphatic or aromatic diisocyanate and particularly preferably composed of an aromatic diisocyanate.

Clause 3. The process as in Clause 1 or 2, characterized in that the polyisocyanate is based on tolylene diisocyanate.

Clause 4. The process as in any of the preceding Clauses, characterized in that the addition of the solvent is carried out in at least two stages, wherein the first stage is performed as a continuous dilution.

Clause 5. The process as in any of the preceding Clauses, characterized in that a solids content of ≥30% to ≤90% by weight, preferably ≥50% to ≤85% by weight, particularly preferably ≥55% to ≤75% by weight and very particularly preferably ≥60% to ≤70% by weight is established in the first stage.

Clause 6. The process as in Clause 4 or 5, characterized in that a solids content of ≥10% to ≤80% by weight, preferably ≥15% to ≤65% by weight, particularly preferably ≥20% to ≤50% by weight and very particularly preferably ≥25% to ≤35% by weight is established in the second stage, wherein the solids content established in the first stage is reduced by at least 15% by weight, preferably by at least 25% by weight, in the second stage.

Clause 7. The process as in any of Clauses 3 to 6, characterized in that the polyisocyanate is produced from tolylene diisocyanate by (i) reaction of tolylene diisocyanate to form a polyisocyanate and (ii) removal of the unconverted tolylene diisocyanate down to a residual content of monomeric tolylene diisocyanate of ≤0.5% by weight, preferably ≤0.3% by weight and particularly preferably ≤0.1% by weight based on the total weight of the polyisocyanate composed of tolylene diisocyanate.

Clause 8. The process as claimed in Clause 7, characterized in that the removal of the unconverted tolylene diisocyanate in step (ii) is carried out by means of at least one thermal separation process, preferably by means of at least one two-stage thermal separation process and particularly preferably by means of at least one falling film evaporator and/or at least one thin film evaporator.

Clause 9. The process as in Clause 8, characterized in that the at least one thermal separation process is performed at a heating medium temperature of ≥140° C.≤ to 235° C. and preferably of ≥160° C. to ≤215° C.

Clause 10. The process as in any of Clauses 7 to 9, characterized in that the polyisocyanate composed of tolylene diisocyanate is an isocyanate-containing polyisocyanurate composed of tolylene diisocyanate, wherein the reaction of tolylene diisocyanate in step (i) to form isocyanurate groups is carried out in the presence of at least one catalyst and terminated at a content of isocyanate groups of ≥30% to ≤46% by weight, preferably of ≥34% to ≤44% by weight and particularly preferably of ≥38% to ≤42% by weight by addition of at least one catalyst poison.

Clause 11. The process as in any of Clauses 7 to 10, characterized in that the steps (i) and (ii) are performed in the presence of ≥0% to <1% by weight of distillation aids that are inert under distillation conditions, liquid and have a boiling point at least 50t higher than that of tolylene diisocyanate and/or ≥0% to <1% by weight based on the total weight of the compounds employed in step (i) and (ii) of compounds comprising one or more hydroxyl groups.

Clause 12. The process as in any of the preceding Clauses, characterized in that addition of the at least one isocyanate-inert solvent to the at least one polyisocyanate is followed in a further step by addition of at least one polyisocyanate composition composed of tolylene diisocyanate which is distinct from the polyisocyanate of the preceding claims, preferably at least one polyisocyanurate composition composed of tolylene diisocyanate and/or at least one polyurethane composition composed of tolylene diisocyanate, and optionally by addition of one or more assistant and additive substances.

Clause 13. A polyisocyanate composition produced or producible by a process of any of Clauses 1 to 12, wherein the polyisocyanate is based on 1,5-diisocyanatopentane (PDI), 2-methyl-1,5-diisocyanatopentane, 1,5-diisocyanato-2,2-dimethylpentane, 1,10-diisocyanatodecane, 2,4- and 2,6-diisocyanato-1-methylcyclohexane, 2,4'-diisocyanatodicyclohexylmethane, 1-isocyanato-1-methyl-4(3)isocyanatomethylcyclohexane, bis(isocyanatomethyl)norbornane, 1,3- and 1,4-bis(isocyanatomethyl)benzene (XDI), 1,3- and 1,4-bis(2-isocyanato-prop-2-yl)benzene (TMXDI), tolylene diisocyanate (TDI), 2,4'- and 4,4'-diisocyanatodiphenylmethane (MDI), 1,5-diisocyanatonaphthalene or 1,3- and 1,4-phenylene diisocyanate or any desired mixtures of these diisocyanates.

Clause 14. The use of the continuous dilution in the dissolution of polyisocyanates, preferably of polyisocyanates composed of tolylene diisocyanate, for preventing cloudiness in the polyisocyanate composition.

Clause 15. The use of a polyisocyanate composition as in Clause 13 as a crosslinking agent in an adhesive or in a coating material, preferably in an adhesive.

Clause 16. A two-component system comprising an isocyanate component A) containing at least one polyisocyanate composition as in Clause 13 and an isocyanate-reactive component B) containing at least one isocyanate-reactive compound, preferably at least one hydroxyl-containing polyester.

Clause 17. A composite system produced or producible by curing the two-component system as in Clause 16 applied to at least one substrate.

The invention claimed is:

1. A process for producing a polyisocyanate composition comprising addition of at least one solvent to at least one polyisocyanate based on tolylene diisocyanate, wherein the addition of the solvent is carried out in one or more stages and at least one of these stages is performed as a continuous dilution and wherein the solvent is inert to isocyanate.

2. The process as claimed in claim 1, wherein the addition of the solvent is carried out in at least two stages, wherein the first stage is performed as a continuous dilution.

3. The process as claimed in claim 1, wherein a solids content of ≥30% to ≤90% by weight of the resulting composition is established in the first stage.

4. The process as claimed in claim 2, wherein a solids content of ≥10% to ≤80% by weight is established in the second stage, wherein the solids content established in the first stage is reduced by at least 15% by weight in the second stage.

5. The process as claimed in claim 1, wherein the polyisocyanate is produced by
(i) reaction of tolylene diisocyanate to form a polyisocyanate and
(ii) removal of the unconverted tolylene diisocyanate down to a residual content of monomeric tolylene diisocyanate of ≤0.5% by weight, based on the total weight of the polyisocyanate composed of tolylene diisocyanate.

6. The process as claimed in claim 5, wherein the removal of the unconverted tolylene diisocyanate in step (ii) is carried out by means of at least one thermal separation process.

7. The process as claimed in claim 6, wherein the at least one thermal separation process is performed at a heating medium temperature of ≥140° C. to ≤235° C.

8. The process as claimed in claim 5, wherein the polyisocyanate composed of tolylene diisocyanate is an isocyanate-containing polyisocyanurate composed of tolylene diisocyanate, wherein the reaction of tolylene diisocyanate in step (i) to form isocyanurate groups is carried out in the presence of at least one catalyst and terminated at a content of isocyanate groups of ≥30% to ≤46% by weight by addition of at least one catalyst poison.

9. The process as claimed in claim 5, wherein steps (i) and (ii) are performed in the presence of ≥0% to <1% by weight of distillation aids that are inert under distillation conditions, liquid and have a boiling point at least 50° C. higher than that of tolylene diisocyanate and/or ≥0% to <1% by weight based on the total weight of the compounds employed in step (i) and (ii) of compounds comprising one or more hydroxyl groups.

10. The process as claimed in claim 5, wherein addition of the at least one solvent to the at least one polyisocyanate is followed in a further step by addition of at least one polyisocyanate composition composed of tolylene diisocyanate which is at least one polyisocyanurate composition composed of tolylene diisocyanate and/or at least one polyurethane composition composed of tolylene diisocyanate, and optionally by addition of one or more assistant and additive substances.

11. A process for preventing cloudiness in a polyisocyanate composition, the process comprising inclusion of the process according to claim 1.

* * * * *